(12) United States Patent
Gundry et al.

(10) Patent No.: US 12,220,068 B2
(45) Date of Patent: *Feb. 11, 2025

(54) CUSHIONED DIAPER CHANGING TABLE

(71) Applicant: Pluie, Inc., Lake Forest, IL (US)

(72) Inventors: Adia Gundry, Keller, TX (US); Jacques Laramie, Chicago, IL (US); Michael Rafferty, Madison, WI (US); Brittany Hizer, Hinsdale, IL (US)

(73) Assignee: Pluie, Inc., Lake Forest, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 18/407,249

(22) Filed: Jan. 8, 2024

(65) Prior Publication Data
US 2024/0138593 A1      May 2, 2024

Related U.S. Application Data

(63) Continuation of application No. 17/694,623, filed on Mar. 14, 2022, now Pat. No. 11,864,664, which is a continuation of application No. 17/038,196, filed on Sep. 30, 2020, now Pat. No. 11,272,793, which is a
(Continued)

(51) Int. Cl.
| | |
|---|---|
| *A47D 15/00* | (2006.01) |
| *A47D 3/00* | (2006.01) |
| *A47D 5/00* | (2006.01) |
| *A61L 2/10* | (2006.01) |
| *B08B 7/00* | (2006.01) |

(Continued)

(52) U.S. Cl.
CPC ............... *A47D 15/00* (2013.01); *A47D 5/00* (2013.01); *A47D 5/003* (2013.01); *A47D 5/006* (2013.01); *A61L 2/10* (2013.01); *B08B 7/0057* (2013.01); *F21V 7/04* (2013.01); *F21V 23/0471* (2013.01); *A47D 3/00* (2013.01); *A61L 2202/11* (2013.01); *A61L 2202/14* (2013.01); *B08B 7/0035* (2013.01)

(58) Field of Classification Search
CPC .......... A47D 5/003; A47D 5/006; A47D 5/00; A47D 3/00; A47D 11/00; A47D 13/00; A47D 15/00; A47D 15/001; A47D 15/003; A61L 2/10; A61L 2202/11; A61L 2202/14; B08B 7/0057; F21V 7/04; F21V 23/0471
USPC ............................................. 5/655, 652, 947
See application file for complete search history.

(56) References Cited

U.S. PATENT DOCUMENTS 4,573,608 A  * 3/1986 Hansen ................... G07F 17/18
                                                      221/92
4,613,996 A    9/1986 Chase et al.
(Continued)

FOREIGN PATENT DOCUMENTS

| KR | 101726646 | | 4/2017 |
|---|---|---|---|
| WO | 2022072499 | A1 | 4/2022 |
| WO | 2023056050 | A1 | 4/2023 |

*Primary Examiner* — Robert G Santos
(74) *Attorney, Agent, or Firm* — Vedder Price P.C.

(57) ABSTRACT

A changing table comprises a wall assembly and a tray assembly. The wall assembly is capable of mounting to a wall, and the tray assembly is pivotally attached to the wall assembly such that the wall assembly and tray assembly form a changeable angle α in between them. The tray assembly comprises an exterior first surface and an interior second surface. The interior second surface comprises a cushion and is configured to receive an infant.

4 Claims, 15 Drawing Sheets

Related U.S. Application Data continuation-in-part of application No. 16/504,963, filed on Jul. 8, 2019, now Pat. No. 10,952,542.

(51) Int. Cl.
*F21V 7/04* (2006.01)
*F21V 23/04* (2006.01)

(56) References Cited

U.S. PATENT DOCUMENTS

| | | | |
|---|---|---|---|
| 5,056,533 A * | 10/1991 | Solano | A61G 7/1023 |
| | | | 5/655 |
| 5,086,527 A * | 2/1992 | Takahashi | A47D 5/003 |
| | | | 108/42 |
| D326,384 S * | 5/1992 | Burt | D6/555 |
| 5,754,999 A | 5/1998 | Helmsderfer | |
| 5,864,905 A | 2/1999 | Helmsderfer | |
| 5,906,015 A * | 5/1999 | Hilger | A47D 5/006 |
| | | | 5/655 |
| 6,389,624 B1 | 5/2002 | Madole | |
| D601,843 S | 10/2009 | Cherry et al. | |
| D605,886 S | 12/2009 | Cherry et al. | |
| 7,891,034 B2 * | 2/2011 | Smith | A47D 5/006 |
| | | | 5/655 |
| 8,365,328 B2 | 2/2013 | Babikian et al. | |
| 9,265,356 B2 | 2/2016 | Glazman | |
| 9,339,571 B2 | 5/2016 | Bilenko et al. | |
| 9,381,125 B2 | 7/2016 | Herbst et al. | |
| 9,615,983 B2 | 4/2017 | Stryker et al. | |
| 9,907,869 B2 | 3/2018 | Bilenko et al. | |
| 10,207,936 B2 | 2/2019 | Duvall et al. | |
| 10,456,488 B2 | 10/2019 | Bilenko et al. | |
| 10,470,955 B2 | 11/2019 | Zerhusen et al. | |
| 10,866,484 B2 | 12/2020 | Lin et al. | |
| 10,952,542 B2 | 3/2021 | Gundry et al. | |
| 11,272,793 B2 | 3/2022 | Gundry et al. | |
| 11,864,664 B2 * | 1/2024 | Gundry | A47D 5/006 |
| 2005/0160528 A1 | 7/2005 | Clark et al. | |
| 2010/0138995 A1 * | 6/2010 | Smith | A47D 5/006 |
| | | | 5/655 |
| 2013/0117936 A1 | 5/2013 | Stryker et al. | |
| 2013/0227787 A1 | 9/2013 | Herbst et al. | |
| 2014/0208511 A1 | 7/2014 | Glazman | |
| 2015/0250907 A1 | 9/2015 | Bilenko et al. | |
| 2016/0151523 A1 | 6/2016 | Bilenko et al. | |
| 2017/0240437 A1 | 8/2017 | Duvall et al. | |
| 2018/0271729 A1 | 9/2018 | Zerhusen et al. | |
| 2019/0030196 A1 | 1/2019 | Bilenko et al. | |
| 2019/0291151 A1 | 9/2019 | Cornelissen et al. | |
| 2020/0073199 A1 | 3/2020 | Lin et al. | |
| 2021/0007505 A1 | 1/2021 | Gundry et al. | |
| 2021/0007510 A1 | 1/2021 | Gundry et al. | |
| 2022/0202203 A1 | 6/2022 | Gundry et al. | |
| 2023/0098564 A1 | 3/2023 | Gundry et al. | |
| 2024/0138593 A1 * | 5/2024 | Gundry | A61L 2/10 |

* cited by examiner

CUSHIONED DIAPER CHANGING TABLE

CROSS REFERENCE TO RELATED APPLICATIONS

This application is a continuation of prior application Ser. No. 17/694,623, filed Mar. 14, 2022 and now U.S. Pat. No. 11,864,664, which was a continuation of prior application Ser. No. 17/038,196, filed Sep. 30, 2020 and now U.S. Pat. No. 11,272,793, which was a continuation-in-part of prior application Ser. No. 16/504,963, filed Jul. 8, 2019 and now U.S. Pat. No. 10,952,542, the disclosures of which are hereby incorporated by reference in their entirety.

FIELD OF THE DISCLOSURE

The disclosure relates to a diaper changing table. More specifically, the disclosure relates to a changing table that is comfortable, convenient, and self-cleaning.

BACKGROUND

A diaper changing table is a platform designed to allow a person to change infant's diaper. Changing tables are widely installed at homes, restaurants, stadiums, public transportations, hotels, shopping centers, etc. United States federal laws require changing tables be installed in all publicly accessible restrooms of federal buildings.

A diaper changing table normally has a raised surface for receiving an infant, allowing the caretaker to change the diaper. Current diaper changing tables have a surface of hard plastic. Such hard plastic is not comfortable and causes unnecessary anxiety to infants which increases the difficulties in changing the diaper. Embodiments disclosed herein provide soft contact receiving surfaces that do not cause discomfort to infants.

Current changing tables provide no hook or loop solution that allow a parent to hang personal accessories, e.g., handbags, when both hands of the parent are busy changing the diaper. This is inconvenient for the parent because the handbags or other personal accessories need to be placed on floors while the floors in public restrooms are not likely to be clean. Embodiments disclosed herein provide multifunctional hook and loop solutions that allow handbags or personal accessories to be hung.

Another issue of current changing tables is that, after repeated use, the infant receiving surfaces of the changing tables unavoidably get dirty. Pathogens can grow on the infant receiving surfaces. Embodiments disclosed herein provide mechanisms for self-cleaning.

SUMMARY

The disclosure relates to a diaper changing table. More specifically, the disclosure relates to a changing table that is comfortable, convenient, and self-cleaning.

In this disclosure, the term "changing table" has the same meaning as "diaper changing table." Current changing tables are made with hard plastic which is not comfortable for infants. Embodiments disclosed herein provide extra comfort to infants. In one embodiment, the surface of the diaper changing table that receives infants is made with a foamed cushion. In another embodiment, the foamed cushion forms a concaved surface for receiving the infant. In yet another embodiment, the foamed cushion is removably attached to the tray of the changing table. The foamed cushion is replaceable as needed.

Current diaper changing tables do not provide a hook or loop solution that allows handbag or personal accessories to be hung. Embodiments disclosed herein provide multifunctional hook and/or loop solutions that allow handbags and personal accessories to be hung. In one embodiment, the changing table includes a loop-shaped front handle. The front handle serves as a handle for a user to pull the tray assembly up or down. The front handle also serves as a mechanism for hanging handbags, backpacks, and/or other accessories. In yet another embodiment, the changing table includes at least one side handle. The side handle is also configured in a loop, providing additional places to hang handbags, backpacks, and/or other accessories.

The infant receiving surfaces of current changing tables grow pathogens after repeated use. Embodiments disclosed herein provide self-cleaning functionality by using UV light to deactivate pathogens. In one embodiment, the changing table includes a timer and/or a processor to control the ON/OFF of the UV light source.

In one embodiment, a changing table includes a wall assembly. The wall assembly includes a housing. The housing includes a transparent panel, or transparent windows and a UV light source. The wall assembly includes a reflector for reflecting the UV light. The reflector may be in front of, coplanar with or behind the UV light source. The changing table includes a tray assembly. The tray assembly is pivotally attached to the wall assembly. The tray assembly is connected to the wall assembly through one or more hinges. The tray assembly can turn in relation to the wall assembly. An angle $\alpha$ is formed between the tray assembly and the wall assembly. The tray assembly includes a front panel forming a first surface of the tray assembly, wherein the front panel is flat and solid. In one embodiment, the tray assembly includes a cushion layer forming a second surface of the tray assembly, wherein the second surface is opposite to the first surface, the second surface is a concaved surface configured to receive an infant.

In one embodiment, a changing table may include a controller. The controller may include processor and machine readable memories accessible to the processor. The machine readable memory may store instructions executable by the processor. The processor may execute the instructions and perform various actions.

In one embodiment, a changing table includes a wall assembly. The wall assembly includes a UV light source. The wall assembly includes a tray assembly. The tray assembly is pivotally attached to the wall assembly. The tray assembly is connected to the wall assembly through one or more hinges. The tray assembly can turn in relation to the wall assembly. An angle $\alpha$ is formed between the tray assembly and the wall assembly. The tray assembly may include a cushion layer forming a concaved surface configured to receive an infant. The changing table includes a processor, the processor executes following instructions: receiving an indication that the changing table enters a closed position, wherein the closed position is when the angle $\alpha$ is zero; counting a first time period of the changing table remaining in the closed position, and activating the UV light source when the first time period is longer than a first time threshold.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the concepts and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the disclosed systems and methods, reference is now made to the following descriptions taken in conjunction with the accompanying drawings.

DETAILED DESCRIPTION

Figure 1:
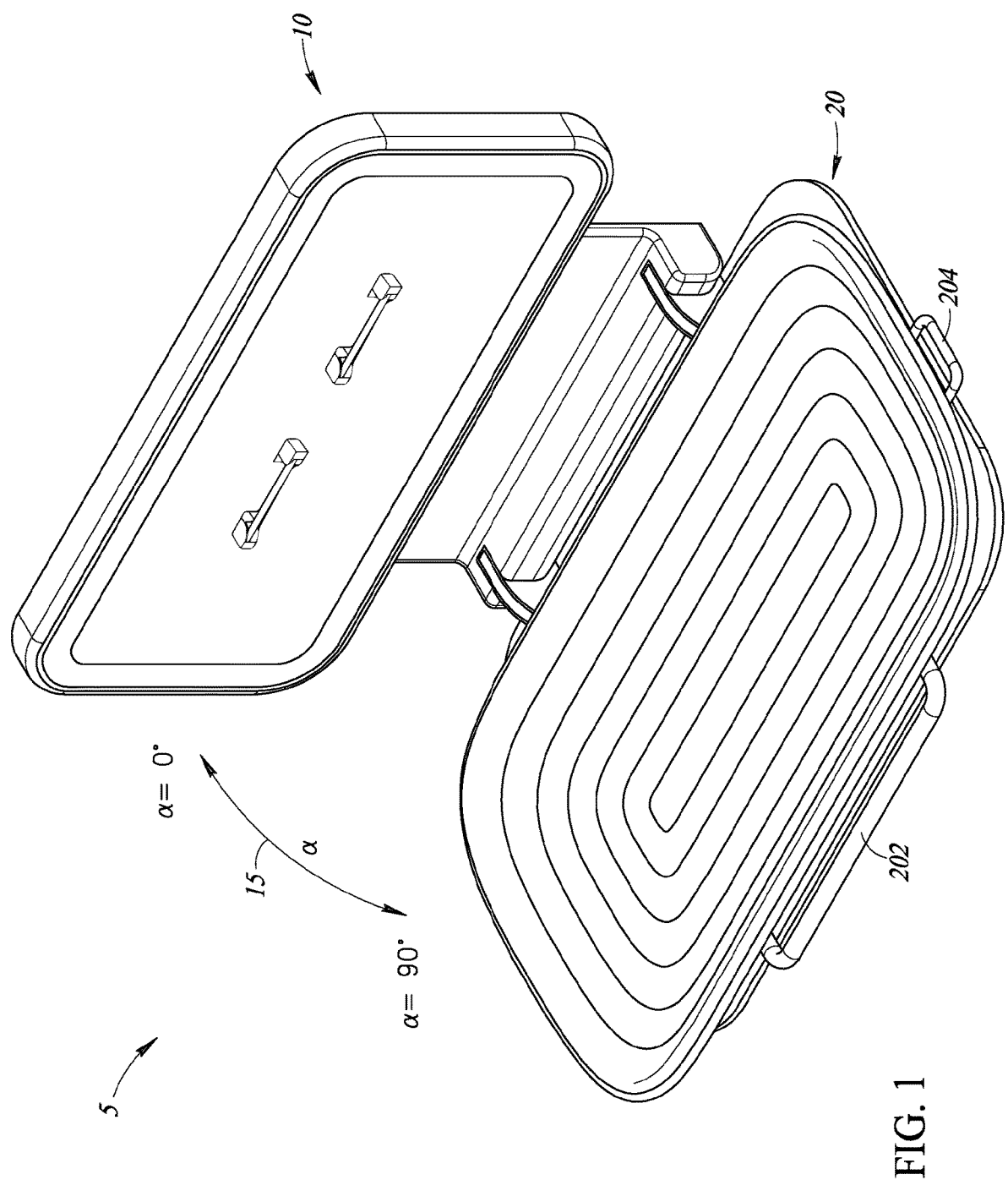
FIG. 1 shows a changing table according to one embodiment of the disclosure.

FIG. 1 shows a changing table 5 according to one embodiment of the disclosure. The changing table 5 includes a wall assembly 10 and a tray assembly 20. The wall assembly 10 can be statically mounted on a wall. The tray assembly 20 is configured to receive an infant.

The tray assembly 20 is pivotally attached to the wall assembly 10. The tray assembly 20 is connected to the wall assembly 10 through hinges, allowing tray assembly 20 to turn in relation to the wall assembly 10. There is an angle α 15 between the tray assembly 20 and the wall assembly 10. As the tray assembly 20 turns in relation to the wall assembly 20, the angle α can change from 0 to 90 degrees. In another embodiment, the tray assembly 20 is connected to the wall assembly 10 through other pivotal and/or turnable means known to a person skilled in the art.

When the angle α 15 is at zero degrees, the tray assembly 20 is in an upright position covering the wall assembly 10. This minimizes the overall volume of the changing table when the changing table is not in use. When the angle α is at zero degrees, the changing table is in a closed position. The closed position is a position when the changing table is not receiving an infant. The UV ray self-cleaning can be performed when the changing table 5 is in the closed position.

When the angle α 15 is at 90 degrees, the tray assembly 20 is lying flat, wherein the concaved surface of the foamed cushion is facing upward ready to receive an infant. When the angle α 15 is at 90 degrees, the changing table is in an open position. In the open position, the changing table does not perform the UV ray self-cleaning.

The tray assembly 20 includes a front handle 202 and a side handle 204. The front handle 202 is located on a front edge of the tray assembly 20. The front handle 202 forms a loop. The front handle 202 can be used by a user to pull down or pull up the tray assembly 20. In one embodiment, a user can use the front handle 202 to pull down the tray assembly 20 from a closed position to an open position. In another embodiment, a user can use front handle 202 to pull up the tray assembly 20 from an open position to a closed position. In another embodiment, the front handle 202 can serve as a hanger for a user to hang a handbag, a cloth, a towel, or any other personal accessory.

The side handle 204 is located on a side edge, perpendicular to the front edge, of the tray assembly 20. The side handle 204 forms a loop. The side handle 204 can be used by a user to pull down or pull up the tray assembly 20. In one embodiment, a user can use the side handle 204 to pull down the tray assembly 20 from a closed position to an open position. In another embodiment, a user can use side handle 204 to pull up the tray assembly 20 from an open position to a closed position. In another embodiment, the side handle 204 can serve as a hanger for a user to hang a handbag, a cloth, a towel, or any other personal accessory. In another embodiment, the tray assembly 20 includes more than one side handle 204, e.g., one on each side.

In one embodiment, the tray assembly 20 includes one or more front handles 202 and/or side handles 204 protruding out of the perimeter of the front panel 210. In one embodiment, the front handles 202 and/or side handles 204 protrude out from the perimeter of the front panel 210 but does not extend beyond the perimeter of the tray 206. In yet another embodiment, the front handles 202 and/or side handles 204 protrude out and extend beyond the perimeter of the tray 206.

Figure 2A:
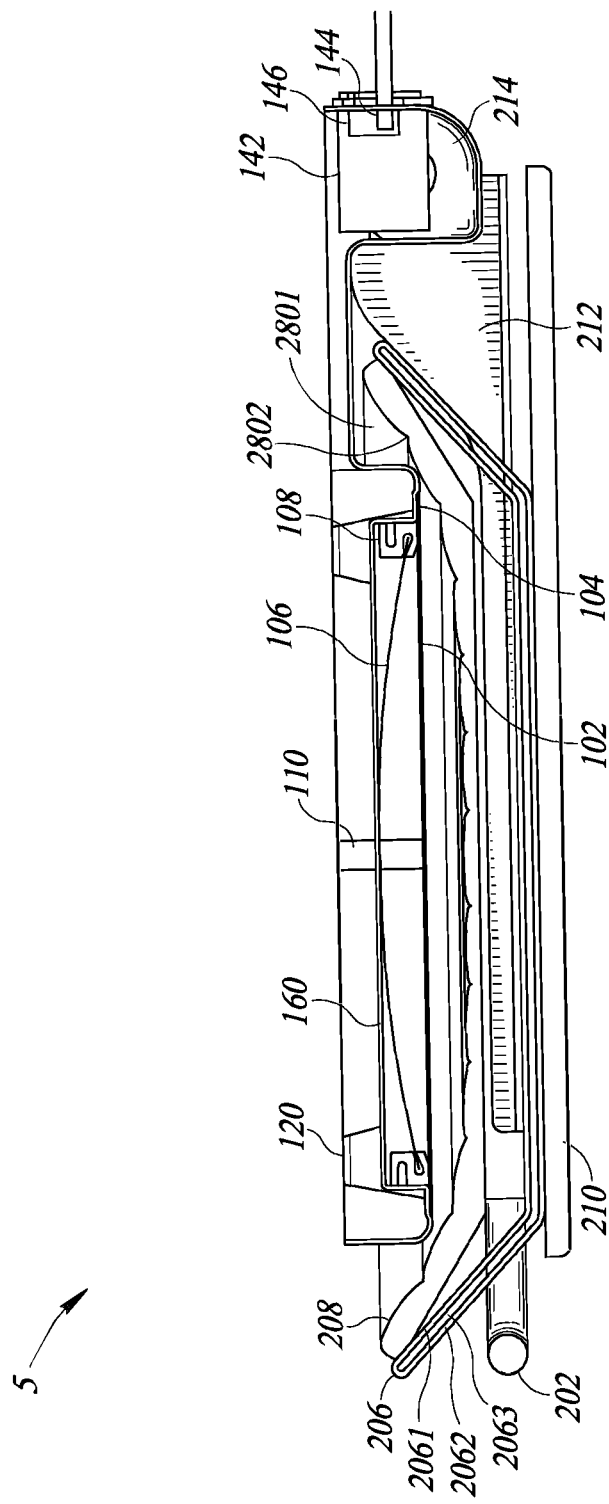
FIG. 2A shows a sectional view of a changing table in a closed position according to one embodiment of the disclosure.

FIG. 2A shows a sectional view of a changing table 500 in a closed position according to one embodiment of the disclosure. In FIG. 2A, the angle α 15 between the tray assembly 20 and the wall assembly 10 is zero. The tray assembly 20 includes at one end surface, a front panel 210. In one embodiment, when the wall assembly 10 is statically mounted on the wall, the front panel 210 is facing away from the wall. In one embodiment, when changing table 5 is in open position, the front panel 210 is facing downward toward the floor. In one embodiment, the front panel 210 is made with a solid material that provides the necessary support for receiving an infant. In one embodiment, the front panel 210 is made with wood or metal.

The tray assembly 20 further includes a tray 206. The tray 206 includes two exterior surfaces. A first exterior surface of the tray 206, at least in part, is in contact with the front panel 210. In one embodiment, the other exterior surface of the tray 206, at least in part, is in contact with the cushion 208. In one embodiment, the tray 206 can be made with a material such as plastic, which is relatively softer than the front panel 210. In yet another embodiment, the tray 206 can be made with a material that is harder than the cushion 208. The tray 206 provides a buffer zone between the cushion 208 and the front panel 210.

As shown in FIG. 2A, the tray 206 includes a top layer 2061, a bottom layer 2062, and a cavity 2063 defined in between. This structure provides the structural support to the cushion 208, yet maintains a level of elasticity when the cushion 208 receives an infant. The tray 206 is in a bowl shape, having a concaved top surface that is, at least in part, in contact with a bottom surface of the cushion 208.

The cushion 208 is the top layer of the tray assembly 20. The cushion 208 is configured to be in contact with the infant. The cushion 208 is made with foam padding materials to provide a soft and comfortable contact with the infant. The cushion 208 has a top surface 2801 which is configured to be in contact with the infant. The top surface 2801 has finishes that are non-porous and hydrophobic, allowing easy cleanings. As shown in FIG. 2A, the cushion 208 includes a plurality of grooves 2802 running circularly and concentrically in parallel on the top surface 2801 of the cushion 208. The grooves 2802 secure the infant when lying on the cushion 208.

In one embodiment, the cushion 208 can be removably attached to the tray 206. The attachment mechanism can be hook-and-loop fasteners (e.g., velcro), adhesives, snap-on fastener, magnets, or the like. The cushion 208 can be replaced when desired. For example, the cushion 208 may be replaced for wear-and-tear and/or dirtiness reasons.

The tray assembly 20 includes tray arm 212. In one embodiment, the tray arm 212 is made with metal, e.g., steel, aluminum, etc. to support the tray assembly. The tray arm 212 is an elongated protrusion disposed between the cushion 208 and the front panel 210. The tray arm 212 includes two ends. The first end of the tray arm 212 includes a hinge 214 connected to the wall assembly 10. The hinge 214 allows the tray assembly 20 to turn in relation to the wall assembly 10, e.g., changing the angle α 15. The second end of the tray arm 212 is connected to an end of the front handle 202. In one embodiment, the tray assembly 20 includes two tray arms 212. In yet another embodiment, the tray assembly 20 may include one, two, or more tray arms 212. Similar to the front handle 202, portions of the one or more side handles 204 are also disposed in the space between the cushion 208 and the front panel 210.

The wall assembly 10 includes a wall housing 120. The wall housing 120 includes a divider 160 that divides the wall housing 120 into a back space and a front space. The back space is proximal to the wall. The front space is distal to the wall compared to the back space.

The back space includes one or more wall mount bar 150 disposed at a back surface (e.g., the surface in contact with the wall) of the wall housing 120. The wall mount bar 150 includes attachment mechanisms, e.g., screw holes, allowing the wall assembly 10 to be mounted on the wall. The front space of the wall housing 120 houses a light assembly 130.

The light assembly 130 includes a transparent panel 102 and a bezel 104 that seals around the transparent panel 102. The light assembly 130 further includes two reflector rails 108. The first reflector rail 108a is disposed proximal to a top side of the transparent panel 102. The second reflector rail 108b is disposed proximal to a bottom side of the transparent panel 102. The light assembly 103 includes one or more UV bulbs 112 and bulb sockets 110 that host and power the UV bulbs 112. The light assembly 130 further includes a reflector 106. The reflector is a curved panel disposed at a back side (e.g., wall side) of the light assembly 130. The reflector panel 106 reflects the UV rays toward the transparent panel 102 (e.g., front side of the light assembly). The reflector panel 106 includes apertures 107 to accommodate the bulb socket 110.

The transparent panel 102 forms a front surface facing the cushion 208 when the changing table 5 is in the closed position. The transparent panel 102 is made with a material, e.g., quartz, fused silica, or other suitable materials that allow UV rays to penetrate through thereof. The transparent panel 102 forms a surface of the wall assembly 10 adjacent to the top surface of the cushion 208 when the changing table 5 is in the closed position.

As shown in the embodiment of FIG. 2A, when the changing table 500 is in the closed position, the tray assembly 20 covers the entire top portion 122 of the wall assembly 10. The top portion 122 of the wall assembly includes the light assembly 130. This means the tray assembly 200 covers enter area of the light assembly 130. In one embodiment, the cushion 208 has a first perimeter. The top portion 122 of the wall assembly 10 has a second perimeter. The first perimeter of the cushion 208 surrounds the entire second perimeter of the top portion 122 of the wall assembly. The first perimeter of the cushion 208 surrounds a third perimeter of the entire light assembly 103.

The design of the tray assembly 20 coving the wall assembly 10 as shown in FIG. 2A includes several benefits in comparison to a design of having the tray assembly 20 being tucked into the wall assembly 10 in a closed position. First, having the perimeter of the tray assembly 20 surrounding the wall assembly 10 maximizes the useable diaper changing surface for the changing table 5. This avoids having a bigger surface of wall assembly 10 that takes up a lot of surface and volume that cannot be used as the diaper changing surface. Second, having the perimeter of the tray assembly 20 surrounding the wall assembly 10 focuses the UV light to the center portion of the tray assembly (where the infant's hip is located), which is the area most actively being contaminated. This avoids wasting the UV light energy shining on the peripheral areas (where the infant's head and feet are located) that are less likely contaminated. The design shown in FIG. 2A may allow using a lower energy output UV light to sufficiently perform the sanitation functionality.

As shown in the embodiment of FIG. 2A, when the changing table 5 is in the closed position, a first concaved surface of the reflector 106 faces a second concaved surface of the cushion 208. The first concaved surface and the second concaved surface face toward each other. The surface area of the second concaved surface of the cushion 208 is greater than the surface area of the reflector 106. In a bird view, the surface area of the second concaved surface of the cushion 208 covers the entire surface area of the reflector 106.

Figure 2B:
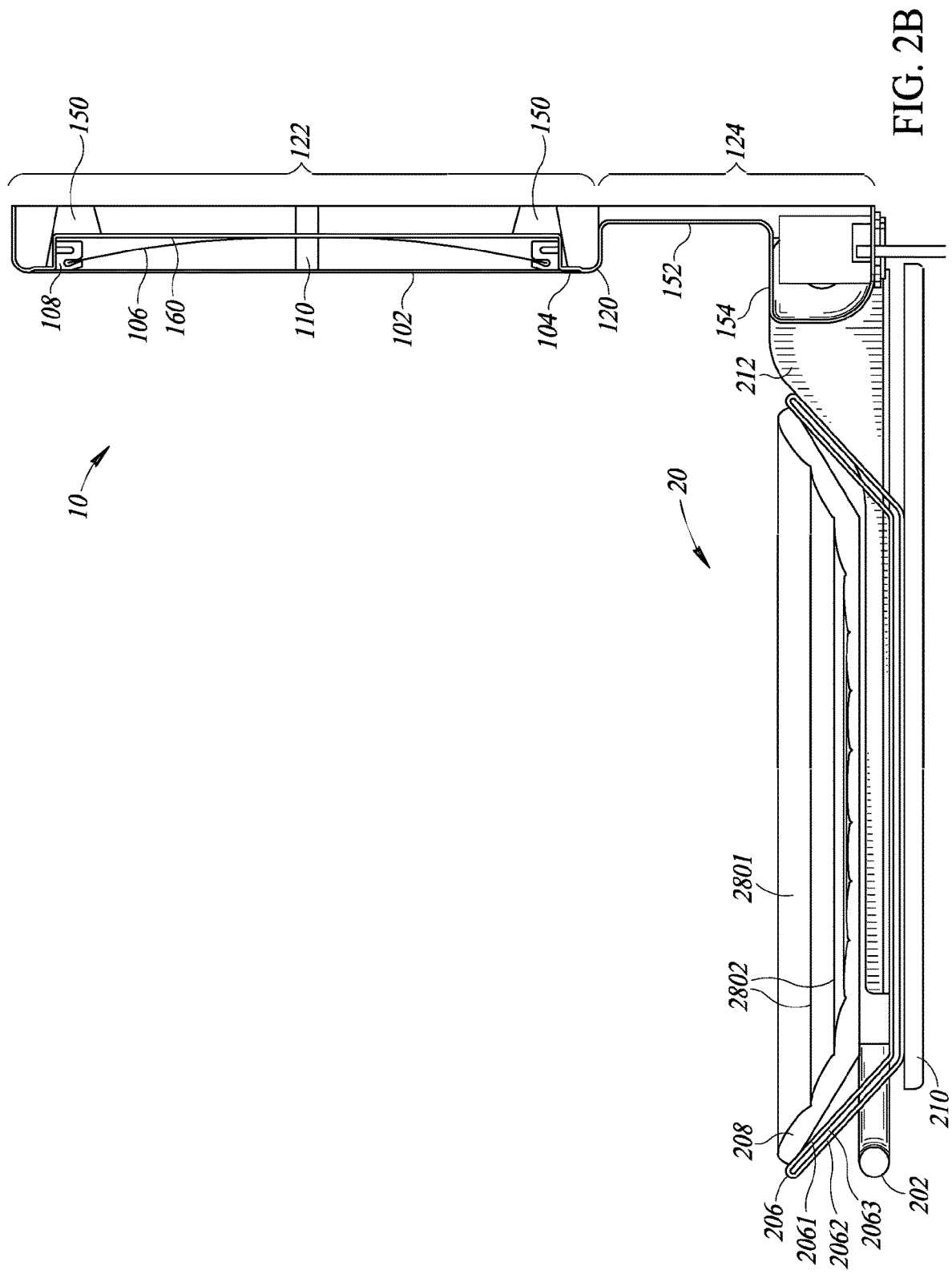
FIG. 2B shows a sectional view of a changing table in an open position according to one embodiment of the disclosure.

FIG. 2B shows a sectional view of a changing table 5 in an open position, angle α 15 is 90 degrees, according to one embodiment of the disclosure. In FIG. 2B, the angle α 15 between the tray assembly 20 and the wall assembly 10 is 90 degrees (open position). The tray assembly 20 includes at one bottom surface, a front panel 210. In one embodiment, when the wall assembly 10 is statically mounted on the wall and the changing table 5 is in open position, the front panel 210 is facing downward. In one embodiment, the front panel 210 is made with solid material that provides the necessary support for the infant. In one embodiment, the front panel 210 is made with wood, hard plastic, or metal.

The tray assembly 20 further includes the tray 206. The tray 206 includes two exterior surfaces. A first exterior surface (e.g., a bottom surface) of the tray 206, at least in part, is in contact with the front panel 210. The other exterior surface (e.g., a top surface) of the tray 206, at least in part, is in contact with the cushion 208. In one embodiment, the tray 206 can be made with a material which is relatively softer than the front panel 210. In yet another embodiment, the tray 206 can be made with a material which is harder than the cushion 208. The tray 206 provides a buffer zone between the cushion 208 and the front panel 210.

As shown in FIG. 2B, the tray 206 includes a top layer 2061, a bottom layer 2062, and a cavity 2063 defined in-between. This structure provides the structural support to the cushion, yet maintains a level of elasticity when the cushion 208 receives an infant. The tray 206 is in a bowl shape, having a concaved top surface that is, at least in part, in contact with a bottom surface of the cushion 208.

The cushion 208 is the top layer of the tray assembly 20. The cushion 208 is configured to be in contact with the infant. The cushion 208 is made with foam padding materials to provide a soft and comfortable contact with the infant. The cushion 208 has a top surface 2801 which is configured to be in contact with the infant. The top surface 2801 has finishes that are non-porous and hydrophobic, allowing easy cleanings. As shown in FIG. 2B, the cushion 208 includes a plurality of grooves 2802 running circularly and concentrically in parallel on the top surface 2801 of the cushion 208. The grooves 2802 increase the frictions between the top surface 2801 and the garment of the infant. The higher frictions better secure the infant when lying on the cushion 208.

In one embodiment, the cushion 208 can be removably attached to the tray 206. The attachment mechanism can be hook-and-loop fasteners (e.g., velcro), adhesives, snap-on fastener, magnets, or the like. The cushion 208 can be replaced when desired. For example, the cushion 208 may be replaced for wear-and-tear and/or dirtiness reasons.

The changing table 5 further includes a wall assembly 10. The wall assembly 10 includes a wall housing 120. The wall housing 120 further includes a top portion 122 and a bottom portion 124.

The top portion 122 of the wall housing 120 includes a divider 160 that divides the wall housing 120 into a back space and a front space. The back space is proximal to the wall. The front space is distal to the wall compared to the back space.

The back space includes one or more wall mount bars 150 disposed at a back surface (e.g., the surface in contact with the wall) of the wall housing 120. The wall mount bars 150 include attachment mechanisms, e.g., screw holes, allowing the wall assembly 10 to be mounted on the wall. The front space of the wall housing 120 houses a light assembly 130.

The light assembly 130 includes a transparent panel 102 and a bezel 104 that seals around the transparent panel 102. The transparent panel 102 is substantially a rectangular shape having four sides, a top side, a bottom side, a left side, and a right side. The light assembly 130 further includes two reflector rails 108. The first reflector rail 108a is disposed proximal to a top side of the transparent panel 102. The second reflector rail 108b is disposed proximal to a bottom side of the transparent panel 102. In yet another embodiment, the two reflector rails 108a and 108b can be installed on the right and left sides.

The light assembly 103 includes one or more UV bulbs 112 and bulb sockets 110 that host and power the UV bulbs 112. The light assembly 130 further includes a reflector 106. The reflector is a curved rectangular panel disposed at a back side (e.g., wall side) of the light assembly 130. The reflector panel 106 reflects the UV rays toward the transparent panel 102 (e.g., front side of the light assembly). The reflector panel 106 includes apertures 107 to accommodate the bulb sockets 110.

The transparent panel 102 forms a front surface facing the cushion 208 when the changing table 5 is in the closed position. The transparent panel 102 is made with a material, e.g., quartz, that allows UV rays to penetrate through thereof. The transparent panel 102 forms a surface of the wall assembly 10 adjacent to the top surface of the cushion 208 when the changing table 5 is in the closed position.

The bottom portion 124 of the wall housing 120 includes a neck portion 152 and a cavity portion 154. The neck portion 152 is in connection to the top portion 122. The cavity portion 154 defines a cavity.

The cavity portion 154 can house a timer 142. In one embodiment, the timer 142 controls the power ON/OFF of the UV light bulb. In one embodiment, the UV light bulb is powered ON, i.e., emitting UV light, only when the changing table is at closed position. This means the UV light bulb is powered ON only when the angle α is at zero degrees. This also means when the angle α is not at zero degrees, the UV light bulb is powered OFF.

In one embodiment, once the changing table 5 is back to the closed position from an open position, the timer 142 is activated. In another embodiment, the timer 142 is not activated until the changing table 5 remains in the closed position for more than a first predetermined period of time, e.g., 1 minute to 5 minutes. The first predetermined period of time is to make sure the changing table 5 is not in use, before the UV light bulb is powered. Once activated, the timer 142 then provides electrical power to the UV light bulb for a second predetermined period of time, e.g., 30 seconds to 10 minutes. The second predetermined period of time is a time for UV ray sanitation. Different time period can be set to effectively deactivate the pathogens.

The cavity portion 154 can house a switch 146. In one embodiment, there is a power switch 146 that is activated and provides electrical power to the UV light bulb only when the angle α is at zero degrees. In one embodiment, the power switch 146 is activated and provides electrical power to the UV light bulb only when the changing table is at the closed position. In one embodiment, when the UV light bulb is on, the tray assembly 20 is locked with the wall assembly 10 and cannot be pulled down. In yet another embodiment, if the tray assembly is pulled down (i.e., angle α 15 is no longer zero), the power to the UV light bulb is immediately cut off.

The cavity portion 154 includes one or more openings 156 for receiving the tray arms 212. The cavity portion 154 further includes a power cord 148.

Figure 3:
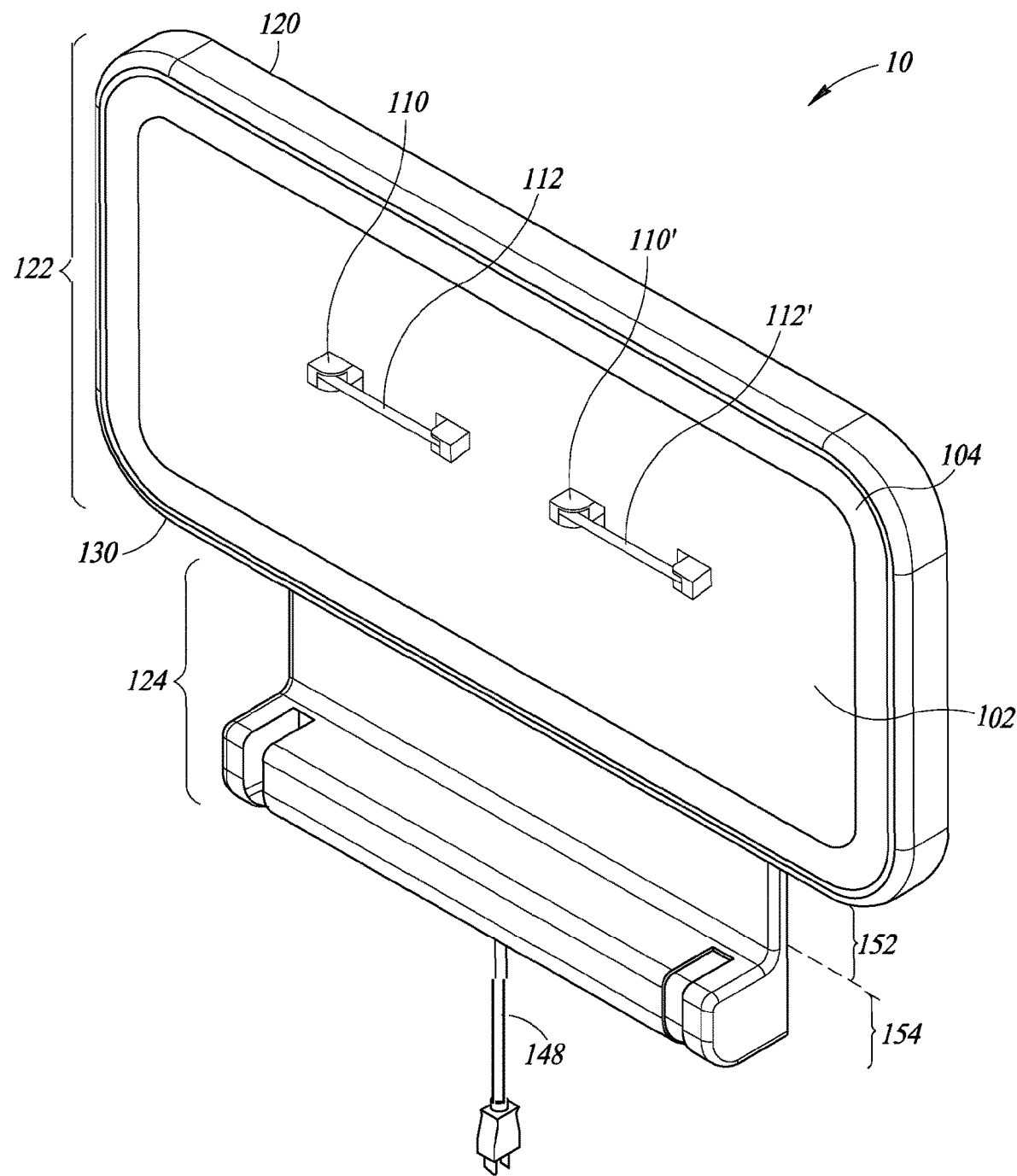
FIG. 3 shows a front perspective view of a wall assembly of a changing table according to one embodiment of the disclosure.

FIG. 3 shows a front view of a wall assembly 10 of a changing table 5 according to one embodiment of the disclosure. The wall assembly 10 includes a wall housing 120. The wall housing 120 further includes a top portion 122 and a bottom portion 124. The top portion 122 of the wall housing 120 includes a divider 160 disposed internally that divides the wall housing 120 into a back space and a front space. The back space is proximal to the wall. The front space is distal to the wall compared to the back space.

The front space of the wall housing 120 houses a light assembly 130. The light assembly 130 includes a transparent panel 102 and a bezel 104 that seals around the transparent panel 102. The transparent panel 102 is substantially a rectangular shape having four sides, a top side, a bottom side, a left side, and a right side.

The light assembly 103 includes one or more UV bulbs 112, 112' and bulb sockets 110, 110' that host and power the UV bulbs 112. The light assembly 130 further includes a reflector 106. The reflector is a curved rectangular panel disposed at a back side (e.g., wall side) of the light assembly 130. The reflector panel 106 reflects the UV rays toward the transparent panel 102 (e.g., front side of the light assembly). The reflector panel 106 includes apertures 107 to accommodate the bulb sockets 110.

The transparent panel 102 forms a front surface facing the cushion 208 when the changing table 5 is in the closed position. The transparent panel 102 is made with a material, e.g., quartz, fused silica, or other suitable materials that allow UV rays to sufficiently penetrate through. The transparent panel 102 forms an exterior surface of the wall assembly 10.

The bottom portion 124 of the wall housing 120 includes a neck portion 152 and a cavity portion 154. The neck portion 152 is in connection to the top portion 122. The cavity portion 154 defines a cavity.

The cavity portion 154 has an internal space that can house a timer 142. In one embodiment, the timer 142 controls the power ON/OFF of the UV light bulb. In one embodiment, the UV light bulb is powered ON, i.e., the UV light bulb emits UV light, only when the changing table is at the closed position. This means the UV light bulb is powered ON only when the angle α is at zero degrees. This means when the angle α is not at zero degrees, the UV light bulb is powered OFF.

In one embodiment, once the changing table 5 is back to the closed position from an open position, the timer 142 is activated. In another embodiment, the timer 142 is not activated until the changing table 5 remains in the closed position for more than a first predetermined period of time, e.g., 1 minute to 5 minutes. The first predetermined period of time is to make sure the changing table 5 is not in use before the UV light bulb is powered ON. Once activated, the timer 142 then provides electrical power to the UV light bulb for a second predetermined period of time, e.g., 30 seconds to 10 minutes. The second predetermined period of time is the time period for UV sanitation. The second predetermined period can be set to most effectively deactivate pathogens.

In one embodiment, as shown in FIG. 3, the UV light bulbs 112, 112' are disposed on a horizontal center line of the top portion 122 of the wall assembly 10 and/or the transparent panel 102 and/or the reflector 106. In yet another embodiment, the one or more UV light bulbs are disposed on a vertical center line of the top portion 122 of the wall assembly 10 and/or the transparent panel 102 and/or the reflector 106.

In one embodiment, when the changing table 5 is in the closed position, a first concaved surface of the reflector 106 faces a second concaved surface of the cushion 208. This means the first concaved surface of the reflector 106 and the second concaved surface of the cushion 208 face toward each other. The surface area of the second concaved surface of the cushion 208 is greater than the surface area of the reflector 106. From a top bird view, the surface area of the second concaved surface of the cushion 208 surrounds the entire surface area of the reflector 106.

The UV light bulbs 112, 112' being disposed at a center line of the transparent panel 102 and/or the reflector 106 allows the UV light to effectively distribute over an actively contaminated area (e.g., hip area of an infant) of the top surface 2801 of the cushion 208, not the peripheral area (e.g., head and feet areas of an infant). In one embodiment, at least a portion of the UV light directed to the top surface 2801 is reflected from the reflector 106. In one embodiment, at least a portion of the UV light is directed to the top surface 2801.

Figure 4:
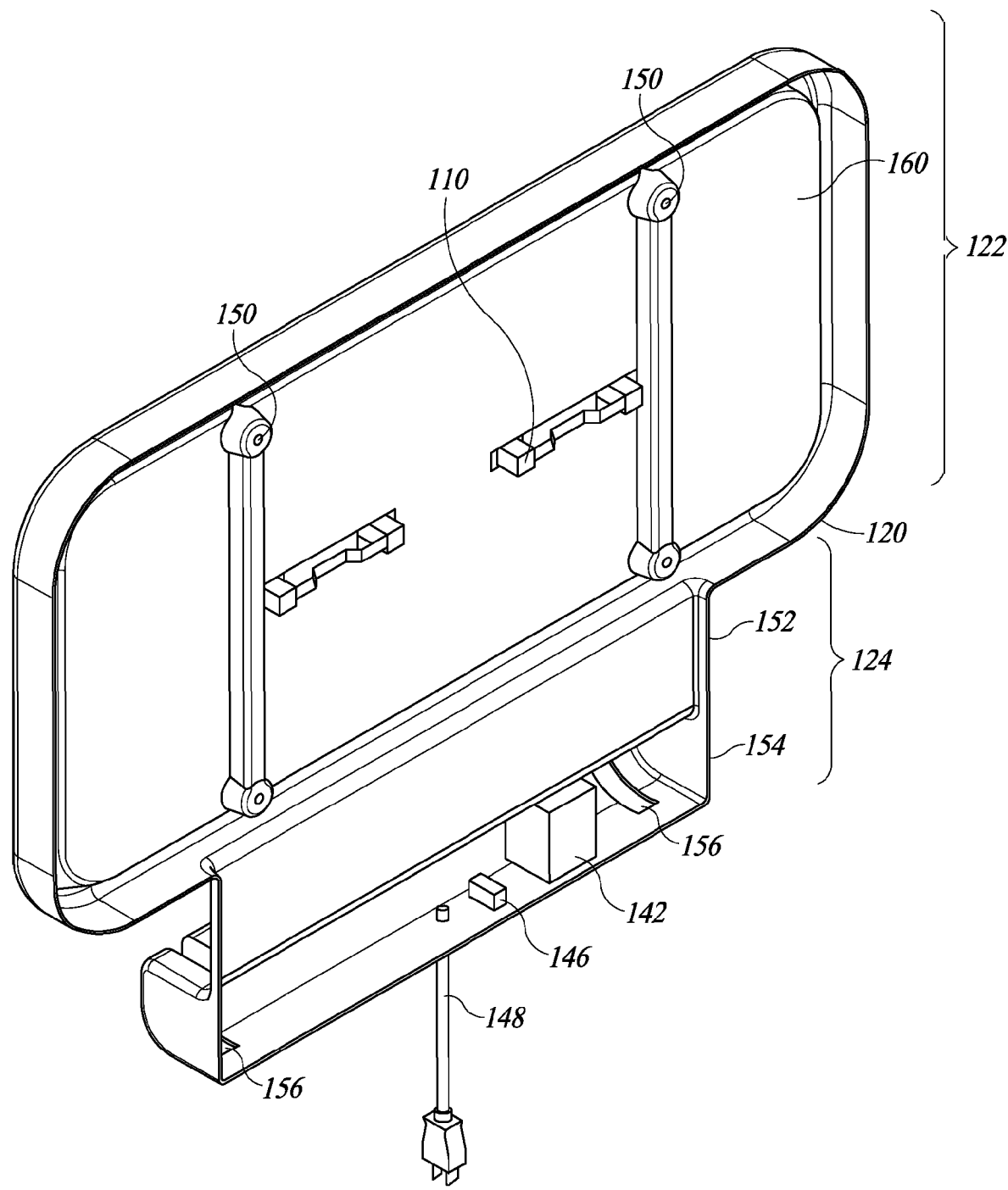
FIG. 4 shows a back perspective view of a wall assembly of a changing table according to one embodiment of the disclosure.

FIG. 4 shows a back view of a wall assembly 10 of a changing table 5 according to one embodiment of the disclosure. The wall assembly 10 includes a wall housing 120. The wall housing 120 includes a top portion 122 and a bottom portion 124.

The top portion 122 of the wall housing 120 includes a divider 160 that divides the wall housing 120 into a back space and a front space. The back space is proximal to the wall. The front space is distal to the wall compared to the back space.

The back space includes one or more wall mount bar 150 disposed at a back surface (e.g., the surface in contact with the wall) of the wall housing 120. The wall mount bar 150 includes attachment mechanisms, e.g., screw holes, allowing the wall assembly 10 to be mounted on the wall. The front space of the wall housing 120 houses a light assembly 130. A portion of the bulb sockets 110 penetrate through the divider 160.

The bottom portion 124 of the wall housing 120 includes a neck portion 152 and a cavity portion 154. The neck portion 152 is in connection to the top portion 122. The cavity portion 154 defines a cavity.

The cavity portion 154 has an internal space that houses a timer 142. In one embodiment, the timer 142 controls the power on/off of the UV light bulb. In one embodiment, the UV light bulb is powered ON, i.e., the UV light bulb emits UV light, only when the changing table is at the closed position. This means the UV light bulb is powered ON only when the angle α is at zero degrees. This means when the angle α is not at zero degrees, the UV light bulb is powered OFF.

In one embodiment, once the changing table 5 is back to the closed position from an open position, the timer 142 is activated. In another embodiment, the timer 142 is not activated until the changing table 5 remains in the closed position for more than a first predetermined period of time, e.g., 1 minute to 5 minutes. The first predetermined period of time is to make sure the changing table 5 is not in use, before the UV light bulb is powered. Once activated, the timer 142 then provides electrical power to the UV light bulb for a second predetermined period of time, e.g., 30 seconds to 10 minutes. The second predetermined period of time is a time for UV ray sanitation. Different time periods can be set to effectively deactivate the pathogens.

The cavity portion 154 also houses a switch 146. In one embodiment, the switch 146 that is activated and provides electrical power to the UV light bulb only when the angle α is at zero degrees. In one embodiment, the switch 146 is activated and provides electrical power to the UV light bulb only when the changing table is at closed position. In one embodiment, when the UV light bulb is ON, the tray assembly 20 is locked with the wall assembly 10 and cannot be pulled down. In yet another embodiment, the if the tray assembly is pulled down (i.e., angle α 15 is no longer zero), the power to the UV light bulb is immediately cut off.

The cavity portion 154 includes one or more openings 156 for receiving the tray arms 212. The cavity portion 154 further includes a power cord 148 that can be plugged into a wall power.

Figure 5:
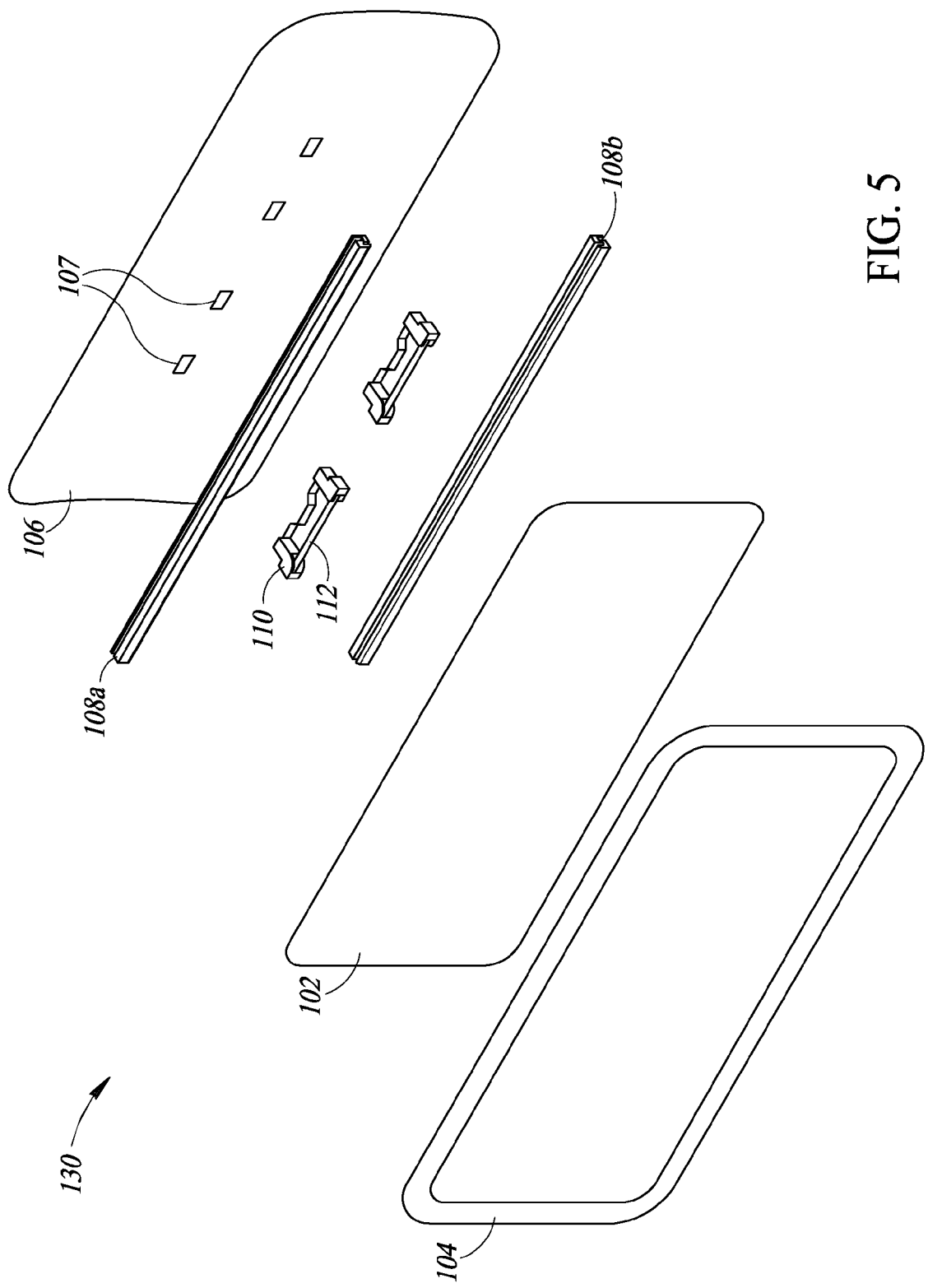
FIG. 5 shows a decomposed view of a light assembly of a changing table according to one embodiment of the disclosure.

FIG. 5 shows a light assembly 130 of a changing table 5 according to one embodiment of the disclosure. The light assembly 130 has a front surface distal to the wall and a back surface proximal to the wall.

The light assembly 130 includes a transparent panel 102 and a bezel that seals around the transparent panel 102. The transparent panel 102 can be at or proximal to the front surface of the light assembly 130. The transparent panel 102 is substantially rectangular, having a top, a bottom, a left, and a right side. The transparent panel 102 is adjacent to the cushion 208 when the changing table 5 is in the closed position. The transparent panel 102 is made with a material, e.g., quartz, that allows UV rays to penetrate through thereof. The transparent panel 102 forms a surface of the wall assembly 10 adjacent to the top surface of the cushion 208 when the changing table 5 is in the closed position.

As shown in FIG. 5, the light assembly 130 further includes two reflector rails 108a, 108b. The first reflector rail 108a is disposed proximal to a top side of the transparent panel 102. The second reflector rail 108b is disposed proximal to a bottom side of the transparent panel 102. In another embodiment, the first reflector rail 108a can be proximal to a right side and the second reflector rail 108b to the left side.

The reflector 106 is installed in the reflector rail 108. The reflector rail 108 hold two sides of the reflector. The reflector 106 forms a curved surface. The reflector 106 is a curved panel disposed at a back side (e.g., wall side) of the light assembly 130. The reflector 106 reflects the UV rays toward the transparent panel 102 (e.g., front side of the light assembly).

One or more UV bulbs 112 are installed in a space between the reflector 106 and the front panel 102. Bulb sockets 110 house and power the UV bulbs 112. The reflector 106 includes apertures 107 to accommodate the bulb socket 110. In another embodiment, the UV bulbs 112 can be a UV emitting solid state light source, e.g., light emitting diode (LED).

Figure 6A:
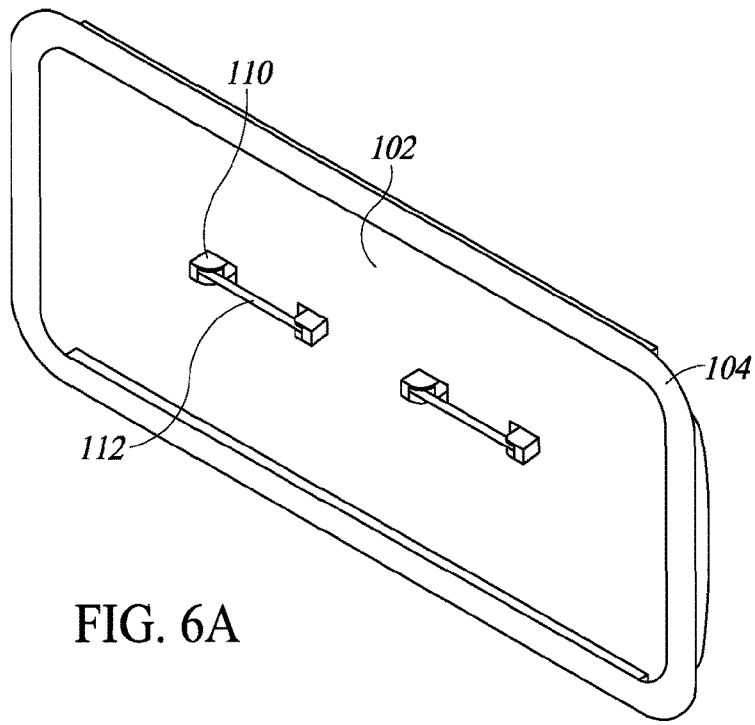
FIG. 6A shows a front view of a light assembly according to one embodiment of the disclosure.

FIG. 6A shows a front perspective view of a light assembly 130 according to one embodiment of the disclosure. FIG. 6A shows the relative positions of the front panel 102, bezel 104, UV light bulbs 112, and bulb sockets 110 in the light assembly 130.

Figure 6B:
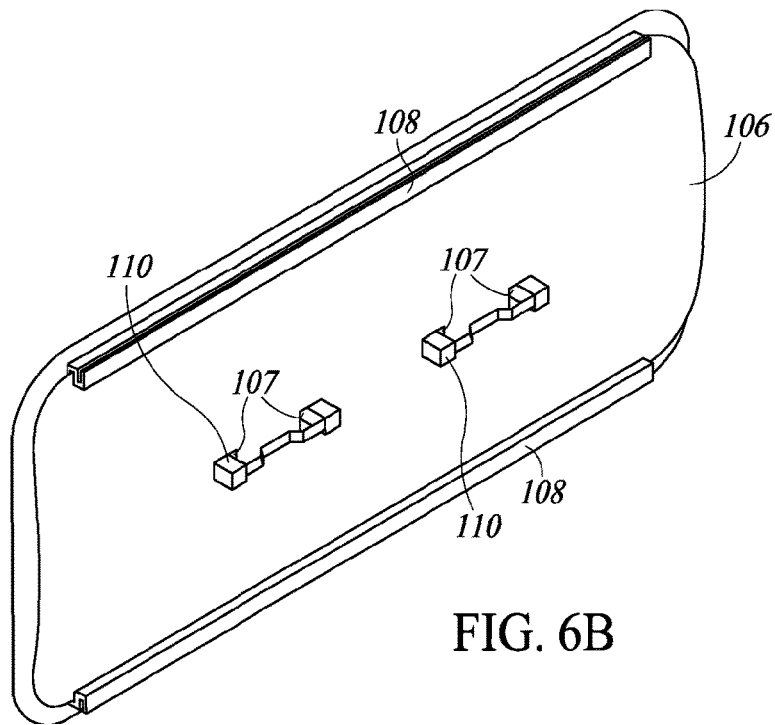
FIG. 6B shows a back view of a light assembly according to one embodiment of the disclosure.

FIG. 6B shows a back view of a light assembly according to one embodiment of the disclosure. FIG. 6B shows the relative positions of the reflector rails 108, reflector 106, and bulb sockets 110 in the light assembly 130. The base of the bulb socket 110 extends through the apertures 107 of the reflector 106.

Figure 6C:
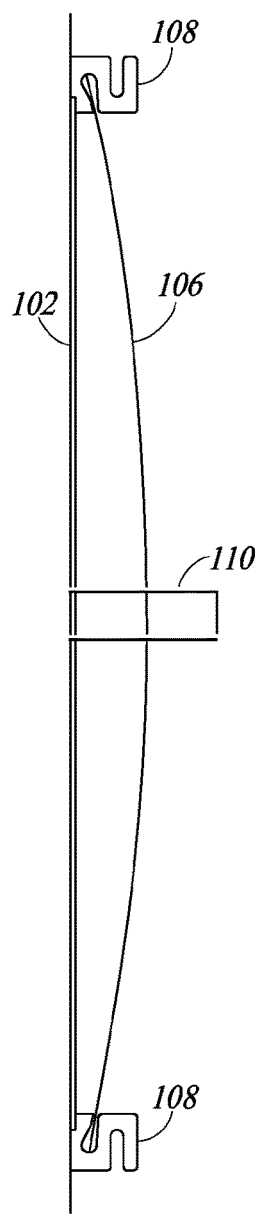
FIG. 6C shows a sectional view of a light assembly according to one embodiment of the disclosure.

FIG. 6C shows a sectional view of a light assembly 130 according to one embodiment of the disclosure. The front panel 102 is disposed at a front surface of the light assembly. A first reflector rail 108 is disposed proximal to a top side of the front panel 102. A second reflector rail 108 is disposed proximal to a bottom side of the front panel 102. The reflector 106 is installed in the reflector rails 108, forming a curved surface. The light bulb 112 is installed between the reflector 106 and the front panel 102.

Figure 7:
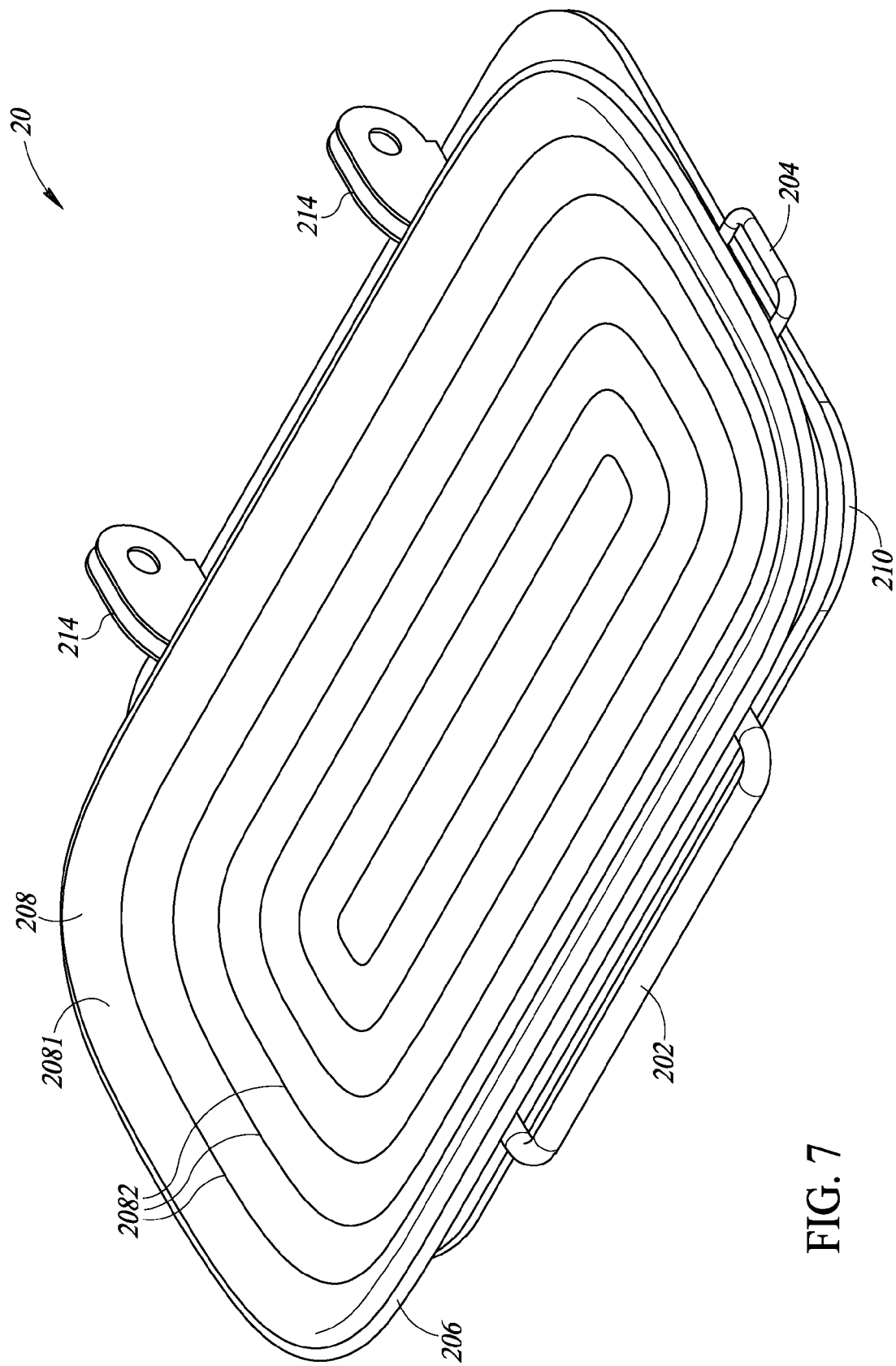
FIG. 7 shows a tray assembly of a changing table according to one embodiment of the disclosure.

FIG. 7 shows a tray assembly 20 of a changing table 5 according to one embodiment of the disclosure. The tray assembly 20 includes at one end surface, a front panel 210. In one embodiment, the front panel 210 is made with a solid material, e.g., wood, hard plastic, metal, that provides the necessary support for the weight of an infant.

The tray assembly 20 includes a tray 206. The tray 206 includes two exterior surfaces. A first exterior surface of the tray 206, at least in part, is in contact with the front panel 210. The other exterior surface of the tray 206, at least in part, is in contact with the cushion 208. In one embodiment, the tray 206 can be made with a material such as plastic which is relatively softer than the front panel 210. In yet another embodiment, the tray 206 can be made with a material such that is harder than the cushion 208. The tray 206 provides a structural buffer between the cushion 208 and the front panel 210. The tray 206 is in a bowl shape, having a concaved top surface that is, at least in part, in contact with a bottom surface of the cushion 208.

The cushion 208 is the top layer of the tray assembly 20. The cushion 208 is configured to be in contact with the infant. The cushion 208 is made with foam padding materials to provide a soft and comfortable contact with the infant. The cushion 208 has a top surface 2801 which is configured to be in contact with the infant. The top surface 2801 has finishes that are non-porous and hydrophobic, allowing easy cleanings. The top surface 2801 with non-porous and hydrophobic finishes does not absorb the infant waste as traditional linen. This allows the infant waste to be easily wiped away from the top surface 2801.

As shown in FIG. 2A, the cushion 208 includes a plurality of grooves 2802 running circularly and concentrically in parallel on the top surface 2801 of the cushion 208. The grooves 2802 secure the infant when lying on the cushion 208. The grooves 2802 increase the frictions between the top surface 2801 and the infant and better secure the infant when lying on the cushion 208.

In one embodiment, the cushion 208 can be removably attached to the tray 206. The attachment mechanism can be hook-and-loop fasteners (e.g., Velcro®), adhesives, snap-on fastener, magnets, or the like. The cushion 208 can be replaced when desired. For example, the cushion 208 may be replaced for wear-and-tear and/or dirtiness reasons.

Figure 8:
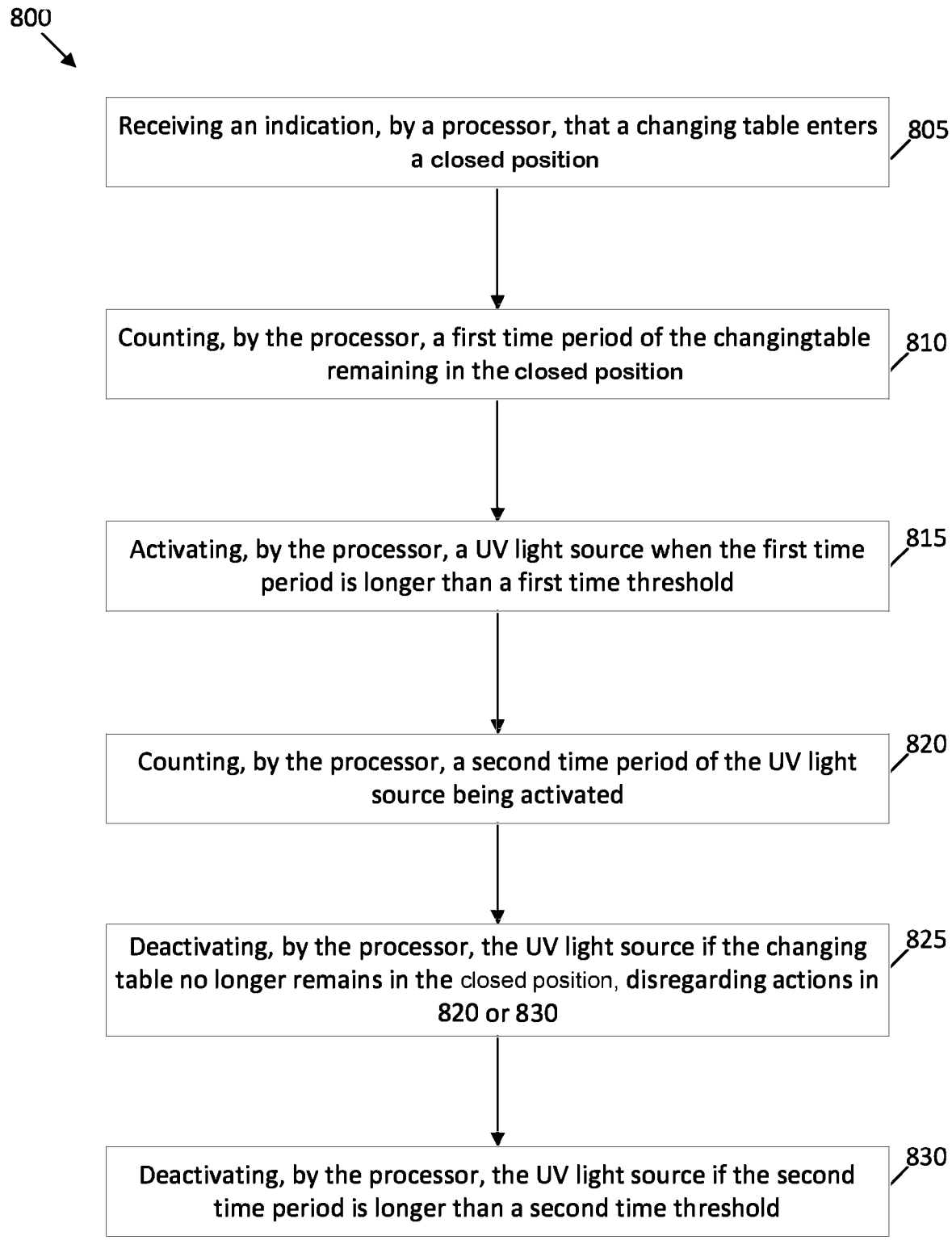
FIG. 8 shows a method for controlling a UV light source according to one embodiment of the disclosure.
Figure 9:
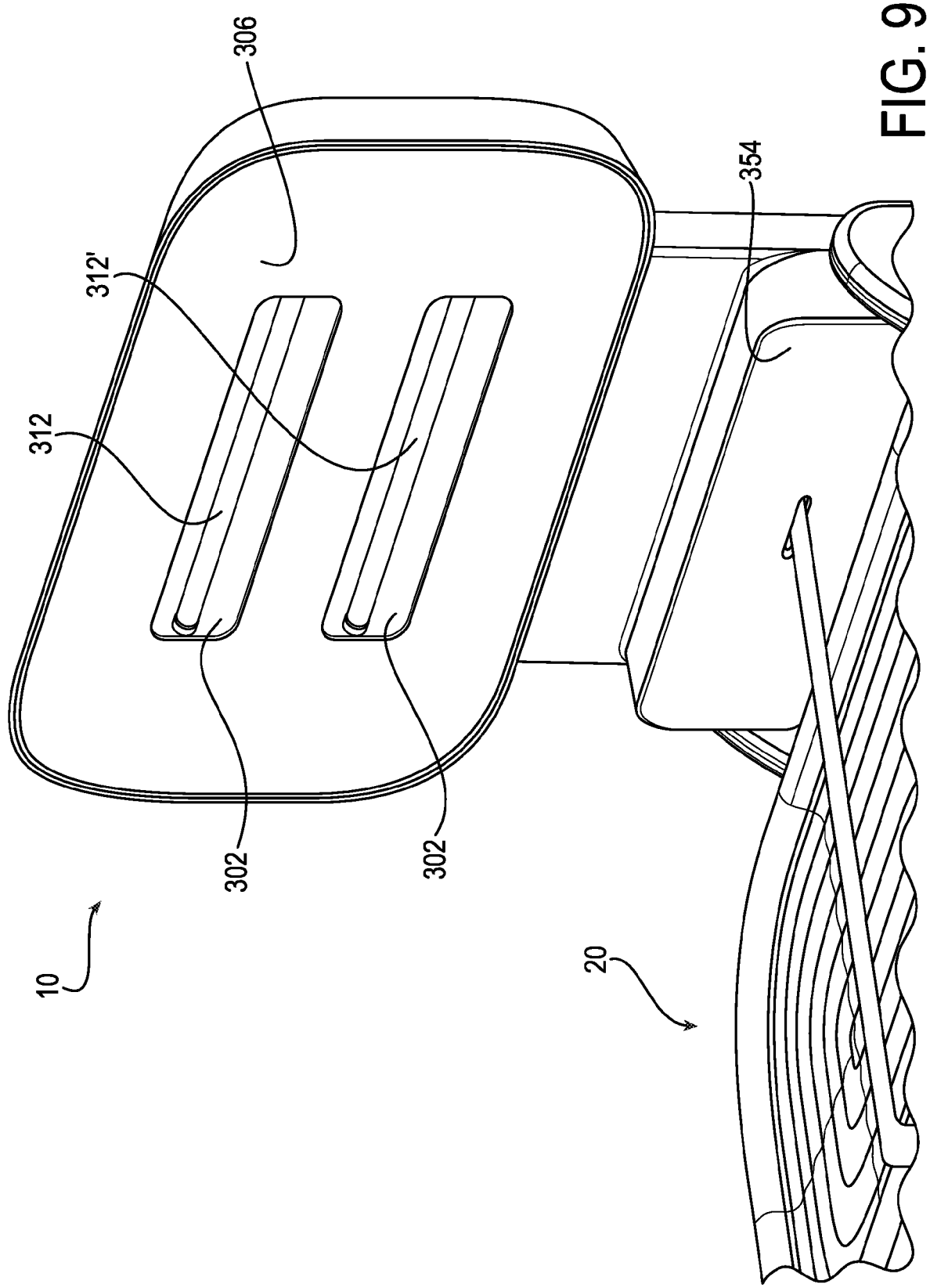
FIG. 9 shows a changing table according to one embodiment of the disclosure.
Figure 10:
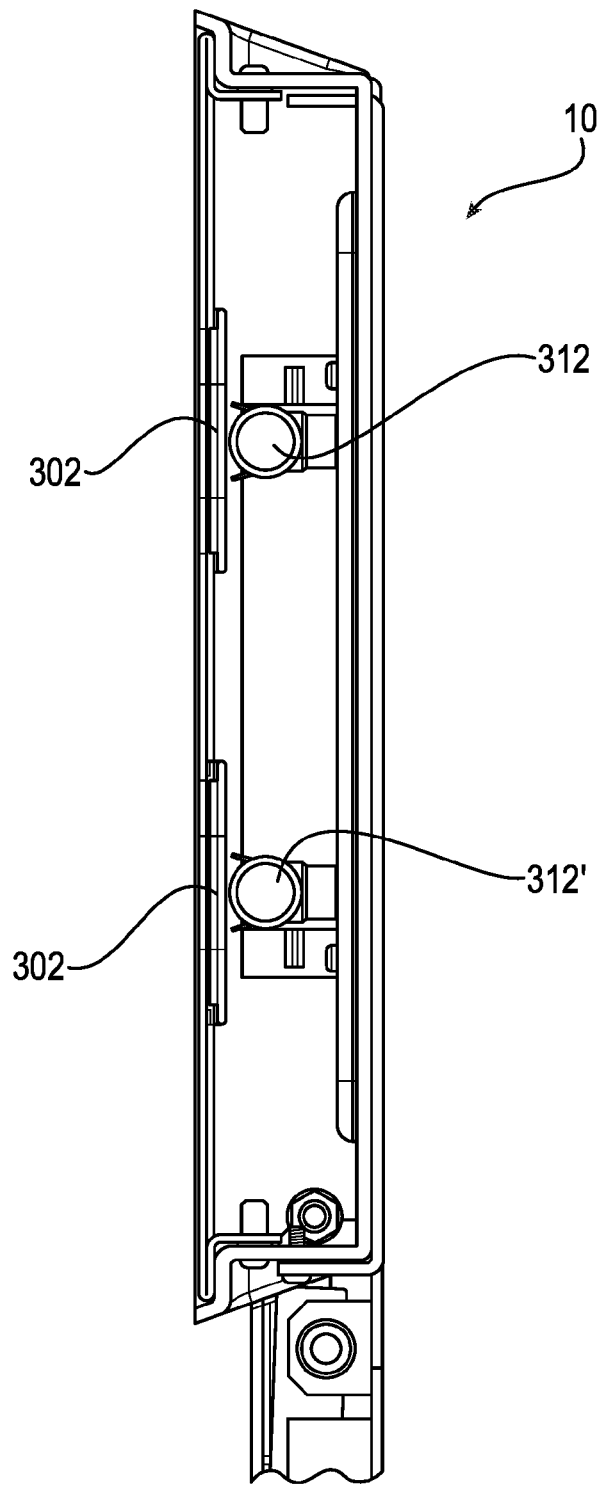
FIG. 10 shows a side sectional view of the changing table of FIG. 9.
Figure 11:
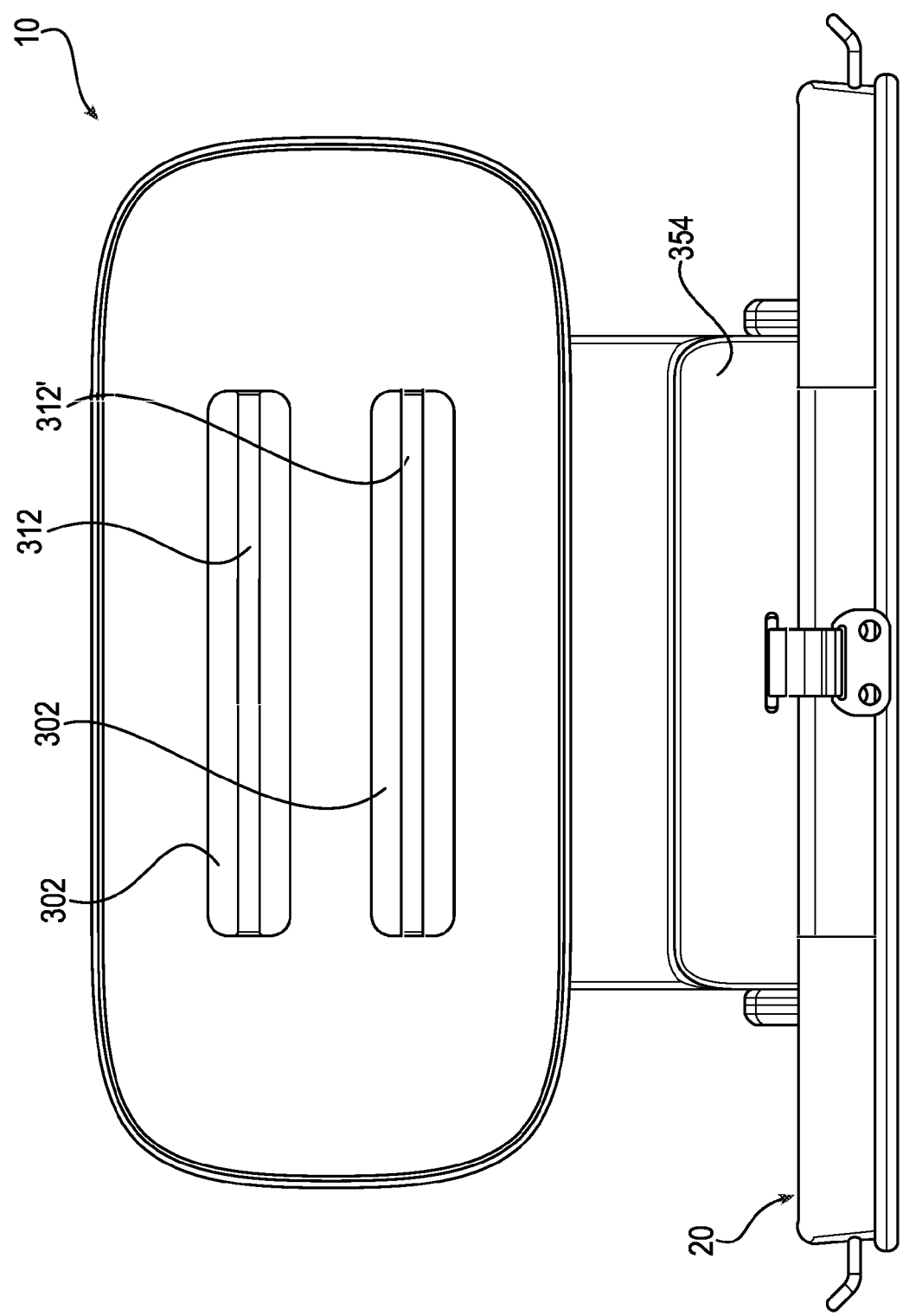
FIG. 11 shows a front view of the changing table of FIG. 9.

FIG. 8 shows a method 800 for controlling a UV light source according to one embodiment of the disclosure. Method 800 can be used in combination with the changing table 5 previously described. The changing table 5 may include a processor to control the activation and deactivation of the UV light source and uses method 800.

In one embodiment, a changing table 5 may include a controller. The controller may include processor and machine readable memories accessible to the processor. The machine readable memory may store instructions executable by the processor. The processor may execute the instructions and perform various actions as described in method 800.

Method 800 includes 805 receiving an indication, by a processor, that a changing table enters a closed position. In one embodiment, there can be a latching mechanism between the tray assembly 20 and wall assembly 10. For example, a protrusion is disposed on the tray assembly 20 and a matching latch is on the wall assembly 10, or vice versa. Only when the protrusion is secured with the matching latch, the method 800 receives the indication that a changing table enters a closed position as 805. In another embodiment, only when the angle α is returned to zero degrees from a non-zero angle, the method 800 receives the indication described in 805.

Method 800 includes 810 counting, by the processor, a first time period of the changing table remaining in the closed position. The first time period is a period to make sure that the changing table is not in use and is ready to receive UV deactivation of pathogens.

Method 800 includes 815 activating, by the processor, a UV light source when the first time period is longer than a first time threshold. After the changing table remains in the closed position long enough, i.e., longer than a first time threshold, the UV light can be activated. In one embodiment, the first time threshold can be from 30 seconds to 10 minutes.

Method 800 includes 820 counting, by the processor, a second time period of the UV light source being activated. At 820, the UV light source is activated to deactivate the pathogen.

Method 800 includes 825 deactivating, by the processor, the UV light source if the changing table no longer remains in the closed position, disregarding the counting of the second time period. The action of 825 is a safety feature making sure no user is exposed to the UV light. In one embodiment, if a user pulls the assembly tray open (e.g., the changing table is no longer in the closed position), the processor will immediately deactivate the UV light source. At 825, the deactivation of UV light source at 825 is irrelevant to the counting of the second time period at 820. At 825, the deactivation of UV light source at 825 is irrelevant to whether the second time period is longer than the second time threshold at 830.

Method 800 includes 830 deactivating, by the processor, the UV light source if the second time period is longer than a second time threshold. The second time threshold is a time period determined to be effective to deactivate the pathogen with the UV light provided by the changing table. In one embodiment, the second time threshold can be from 30 seconds to 10 minutes.

In another embodiment as shown in FIGS. 9-12, the wall assembly 10 includes a reflector 306 is in front of the bulbs 312 and 312'. Transparent windows 302 made of any suitable material such as quartz, fused silica, polymers, or any other suitable material that allows for the transmission of UV light are provided in front of the bulbs 312 and 312' to allow for the UV light to pass through. By placing the reflector 306 and the windows 302 in front of the bulbs 312 and 312', inadvertent contact with the bulbs 312 and 312' is prevented. The UV light from the bulbs 312 and 312' reflects off the tray assembly 20 to the reflector 306 and is returned to the tray assembly 20.

Figure 12:
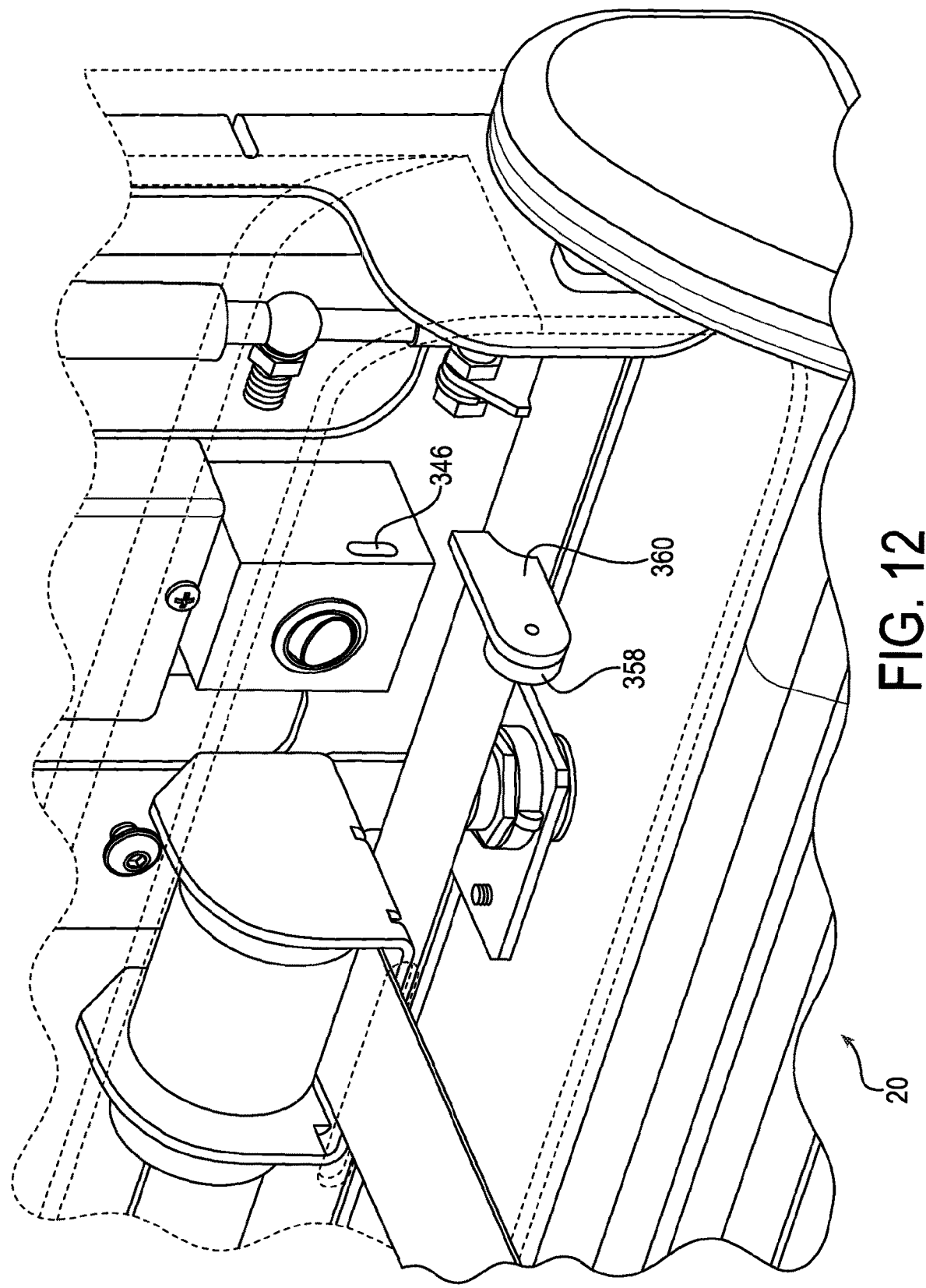
FIG. 12 shows a perspective view of a portion of the changing table of FIG. 9.

As shown in FIG. 12 a switch 346 is located within circuitry housing 354. The switch 346 is activated when the tray assembly 20 is rotated up and closed. In one embodiment a reed switch 346 and magnet 358 mounted on magnet arm 360 may be used. The reed switch 346 is activated by the magnet 358 that is brought in proximity to the reed switch 346 when the tray assembly 20 is rotated upward. Other types of switches may be used in place of the reed switch 346.

Figure 13:
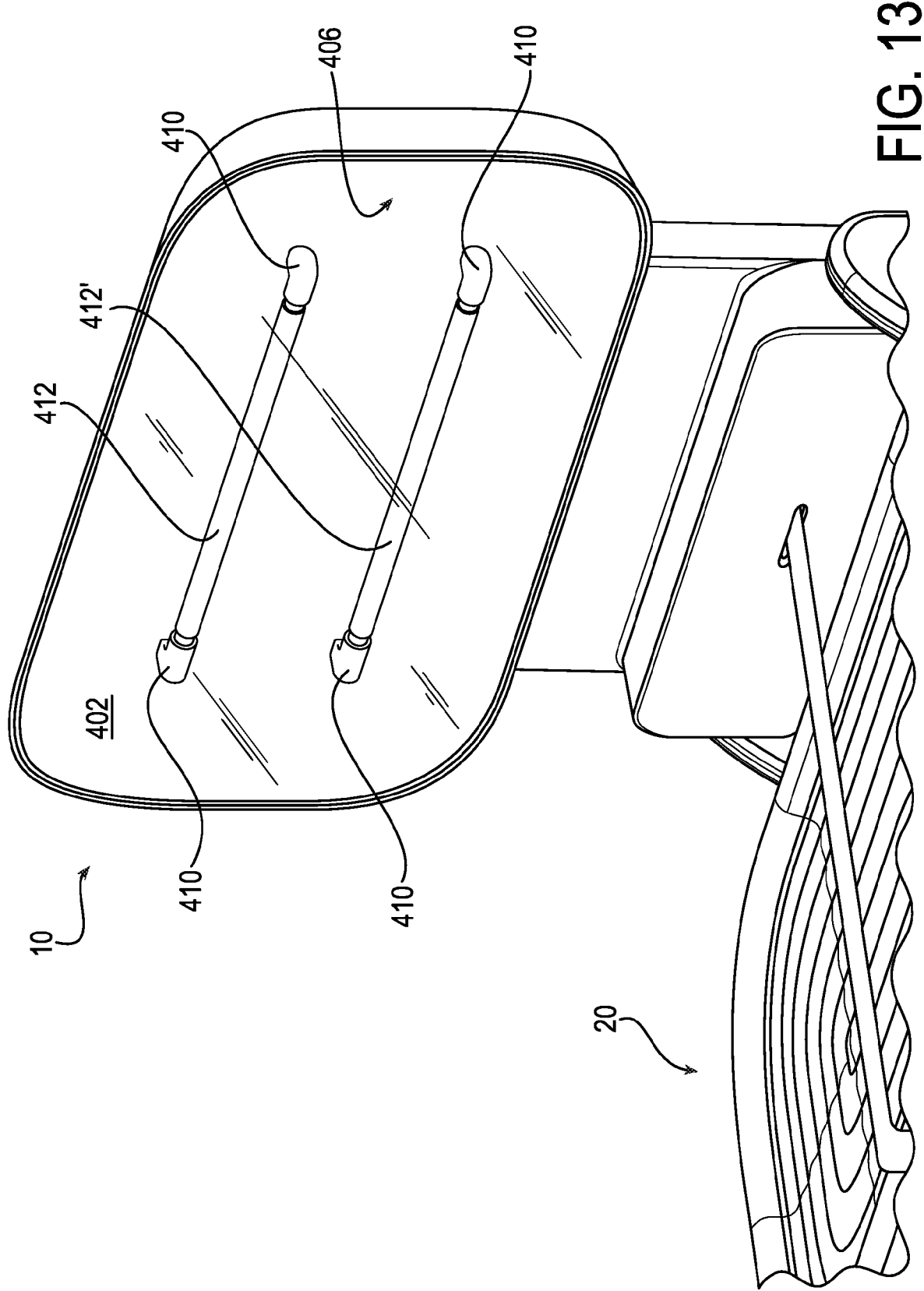
FIG. 13 shows a perspective view of another embodiment of the disclosure.
Figure 14:
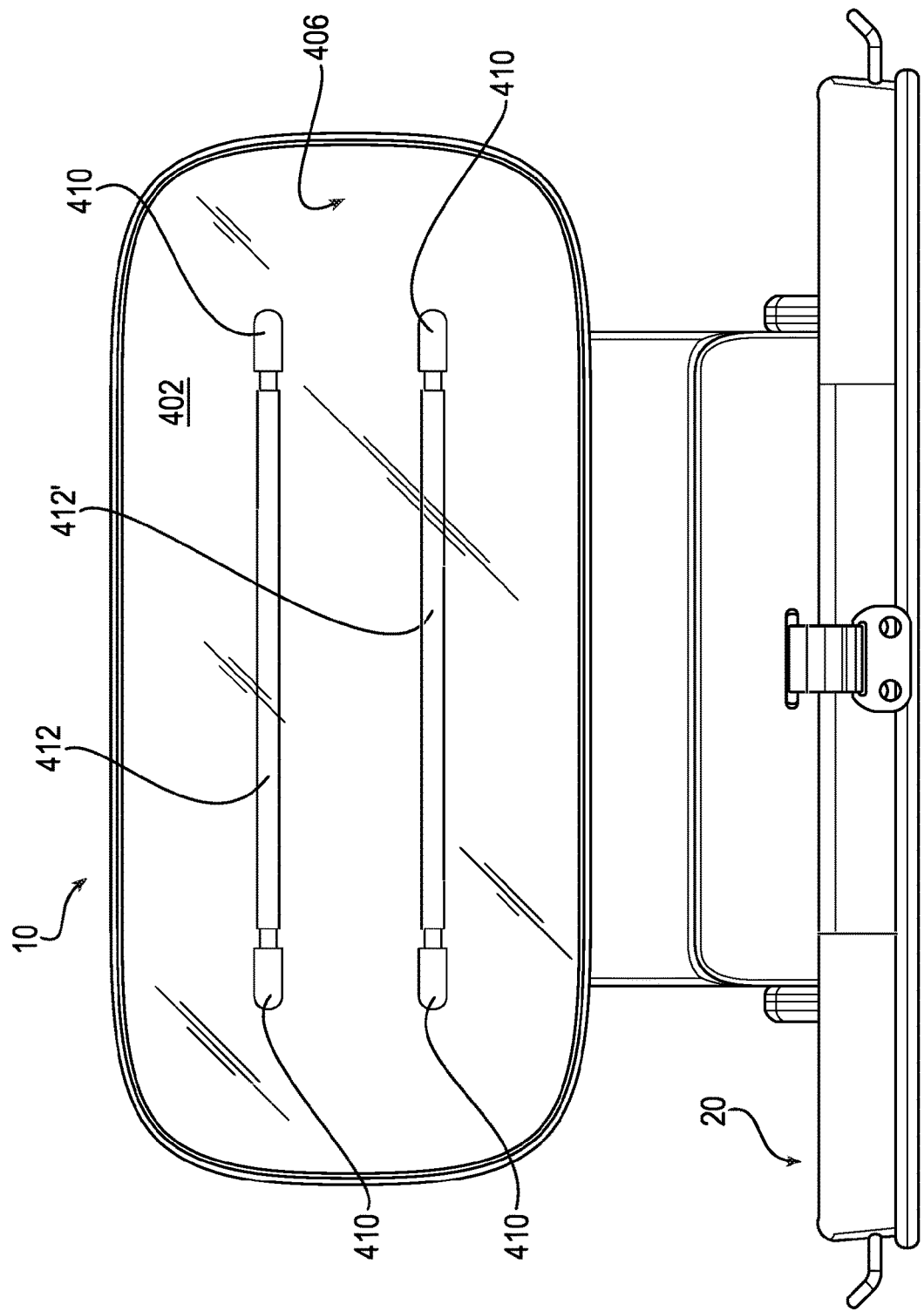
FIG. 14 shows a front view of the embodiment of FIG. 13.

In the embodiment shown in FIGS. 13 and 14, transparent window 402 covers substantially all of the front of the wall assembly 10, although the transparent window 402 could cover a smaller portion of the wall assembly 10. Bulbs 412 and 412' are located behind transparent window 402. Bulb sockets 410 and 410' are mounted to the wall assembly 10 with mounting hardware 410. A reflector 406 is behind the bulbs 412 and 412'.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present invention, disclosure, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A changing table, comprising:
a wall assembly capable of mounting to a wall; and
a tray assembly pivotally attached to the wall assembly;
wherein the tray assembly comprises a cushion; wherein the cushion comprises a top surface comprising a plurality of concentric grooves.

2. A changing table, comprising:
a wall assembly capable of mounting to a wall;
a tray assembly pivotally attached to the wall assembly; and
at least one side handle protruding from a side edge of the tray assembly;
wherein the tray assembly comprises a cushion and wherein at least one side handle forms a loop.

3. A changing table, comprising:
a wall assembly capable of mounting to a wall;
a tray assembly pivotally attached to the wall assembly; and
at least one side handle protruding from a side edge of the tray assembly;
wherein the tray assembly comprises a cushion and wherein at least one side handle extends beyond a perimeter of the tray assembly.

4. A changing table, comprising
a wall assembly capable of mounting to a wall;
a tray assembly pivotally attached to the wall assembly; and
at least one side handle protruding from a side edge of the tray assembly;
wherein the tray assembly comprises a cushion and wherein at least one side handle is graspable when the changing table is in a closed position.

* * * * *